United States Patent [19]

Montgomery

[11] 4,360,972

[45] Nov. 30, 1982

[54] METHOD OF SELECTING ONE OF A PLURALITY OF STANDARD SIZE BURN GLOVES

[75] Inventor: John R. Montgomery, Toledo, Ohio

[73] Assignee: Jobst Institute, Inc., Toledo, Ohio

[21] Appl. No.: 245,590

[22] Filed: Mar. 19, 1981

[51] Int. Cl.³ .............................................. A41H 1/00
[52] U.S. Cl. ..................................... 33/17 R; 128/156
[58] Field of Search .................... 33/17 R, 2 R, 17 A, 33/11, 12, 15, 6; 128/155, 156

[56] References Cited

U.S. PATENT DOCUMENTS 4,136,452  1/1979  McMillan ............................ 33/17 R
4,224,740  9/1980  Gibson ................................ 33/17 A Primary Examiner—William D. Martin, Jr.
Attorney, Agent, or Firm—Wilson, Fraser, Barker & Clemens

[57] ABSTRACT

The invention disclosed concerns a method of selecting a standard glove size. The method includes the steps of selecting a pair of two dimensional measurements which are correlated to hand volume, dividing a population of hand volumes into a predetermined number of approximately equally populated subgroup ranges, plotting two dimensional chart areas for each subgroup based upon intersections of the selected two dimensional measurements with reference to a predetermined point on the chart, and assigning one of the standard sizes to each chart area. The method further includes the steps of placing a hand on the predetermined point and plotting the intersection of the pair of two dimensional measurements for the hand to select the proper standard glove size. The chart can include areas for both left and right hands and the predetermined point can abut the web space between the middle and index fingers on the hand.

6 Claims, 4 Drawing Figures

METHOD OF SELECTING ONE OF A PLURALITY OF STANDARD SIZE BURN GLOVES

BACKGROUND OF THE INVENTION

1. Field of the Invention

The present invention relates to covers for burned hands and in particular to a method for selecting one of a plurality of standard size gloves.

2. Description of the Prior Art

One of the problems associated with burns is hypertropic scarring and edema. It has been found that the application of continuous pressure on hypertropic scar formation controls and/or diminishes the deforming sequelae associated with thermal injuries. One solution to the problem is an elastic bandage wrap. However, it often is difficult to obtain and maintain consistant pressure with such wraps especially in areas of rapidly changing contour such as a hand.

A better solution to the problem is a glove formed from an elastomeric knitted fabric. The glove can be custom fitted to the hand for the precise application of pressure in all areas. However, since the glove is custom fitted, there is a manufacturing delay before the glove is available.

SUMMARY OF THE INVENTION

The present invention concerns a glove for burned hands for use in interim therapy in the treatment regimen for hypertropic scarring and/or edema. The glove is formed from a pair of fabric blanks having finger, thumb and wrist portions connected to a body portion. The edges of the blanks are stitched together leaving the wrist portion open for the insertion of the hand. Cutouts are formed in the web area between adjacent fingers and the edges of the cutouts are stitched together to apply local pressure in the dorsal web areas of the hand. The cutouts are slanted with respect to the longitudinal axes of the adjacent fingers to avoid the knuckle areas of the hand.

In an alternate embodiment, a flap is connected to the body portion of each blank along the little finger edge thereof. The flaps and the edges of the wrist portions of the two blanks are not attached such that they can be separated to provide a large opening for the insertion of the hand. The flaps can be provided with a loop means and a hook means can be utilized to attach the loop means after the flaps have been wrapped about the wrist. The loop and hook means provide for the adjustment of the pressure applied to the wrist.

The present invention also relates to a method of selecting a standard glove size. Two dimensional measurements having a relatively high correlation to hand volume are selected. A population of hands is divided into a predetermined number of approximately equally populated hand volume size ranges by equal subdivision of the area under the associated maximum likelihood normal probability curve. Two dimensional chart areas for each subgroup are then plotted. The hand to be measured is placed on the chart at a predetermined position and a horizontal line and a vertical line are extended from predetermined points on the hand. The intersection of the two lines falls into one of chart areas to select a corresponding glove size.

Further objects and advantages of the invention will become apparent to those skilled in the art from the following detailed description, taken in conjunction with the annexed sheets of drawings, on which is illustrated a preferred embodiment of this invention.

DESCRIPTION OF THE PREFERRED EMBODIMENT

Figure 1:
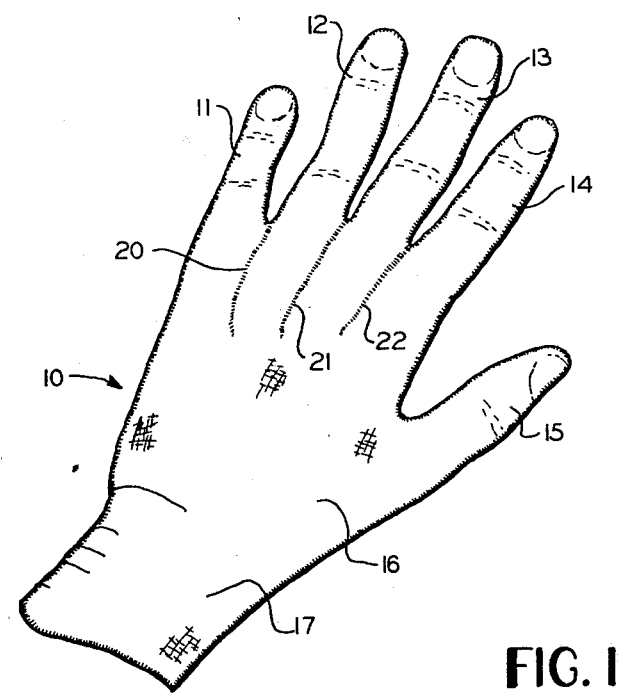
FIG. 1 is a perspective view of a glove according to the present invention fitted to a human hand.

Referring to FIG. 1 there is shown a perspective view of a glove 10 according to the present invention. The glove includes finger portions 11, 12, 13 and 14 and a thumb portion 15 integral with a body portion 16 tapering to a wrist portion 17. The glove 10 is formed from a pair of identical fabric blanks which are sewn together at the edges 18 thereof as shown more clearly in FIG. 2. The outside edges 19 of the wrist portion 17 are not sewn together to permit the insertion of a hand in the glove. However, these edges 19 can be stitched to strengthen them.

The glove 10 is particularly useful in the interim therapy in the treatment regimen for hypertropic scarring and/or edema. The fabric blanks are formed from a knitted elastic fabric and shaped to apply a graduated pressure to the hand. For example, the glove 10 can apply approximately five mm Hg. at the wrist to approximately twenty-five mm Hg. at the finger tips.

A glove for applying graduated pressure in the treatment of hypertropic scarring and/or edema is commercially available as catalog no. 05-35 from Jobst Institute, Inc. However, such a glove must be custom made and, therefor, would not be available for immediate treatment. The glove according to the present invention is constructed from two identical blanks. Therefore, it can be worn on either hand and is relatively inexpensive to manufacture and stock for immediate availability for temporary treatment.

Figure 2:
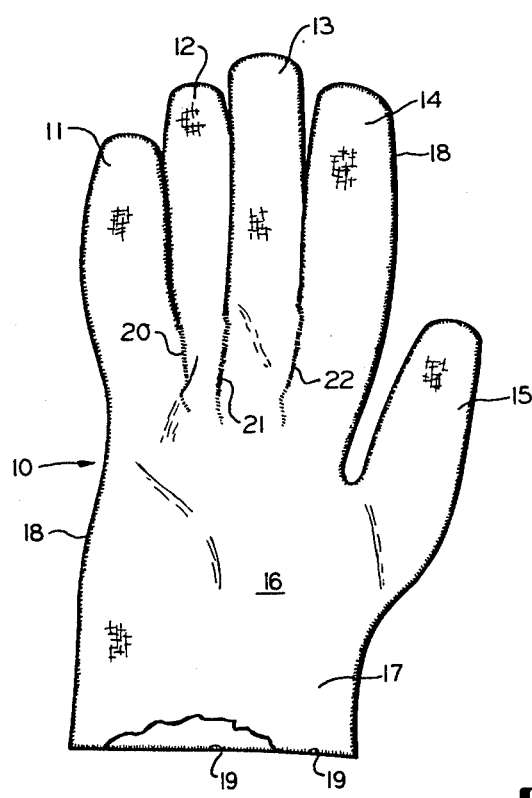
FIG. 2 is a plan view of the glove shown in FIG. 1.

The glove 10 also includes stitching on each blank extending from the web spaces between adjacent pairs of fingers along the body portion 16 toward the wrist portion 17. As shown in FIGS. 1 and 2, stitching 20 extends from the web space between the fingers 11 and 12, stitching 21 extends from the web space between the fingers 12 and 13, and stitching 22 extends from the web space between the fingers 13 and 14. The stitching joins edges formed from tear drop shaped cutouts made in the blanks, the pointed ends of the cutouts oriented toward the web spaces. The joining of these edges stretches the fabric to create local pressure areas over the dorsal web spaces of the hand. Although not shown, the opposite side of the glove 10 has similar stitches. Such local pressure is extremely important in the treatment of burns for preventing the formation of scar tissue. Furthermore, the stitches are slanted with respect to the longitudinal axes of the adjacent fingers to avoid the knuckle areas and the associated tendons which are located there to prevent pressure points from forming ulcers.

Figure 3:
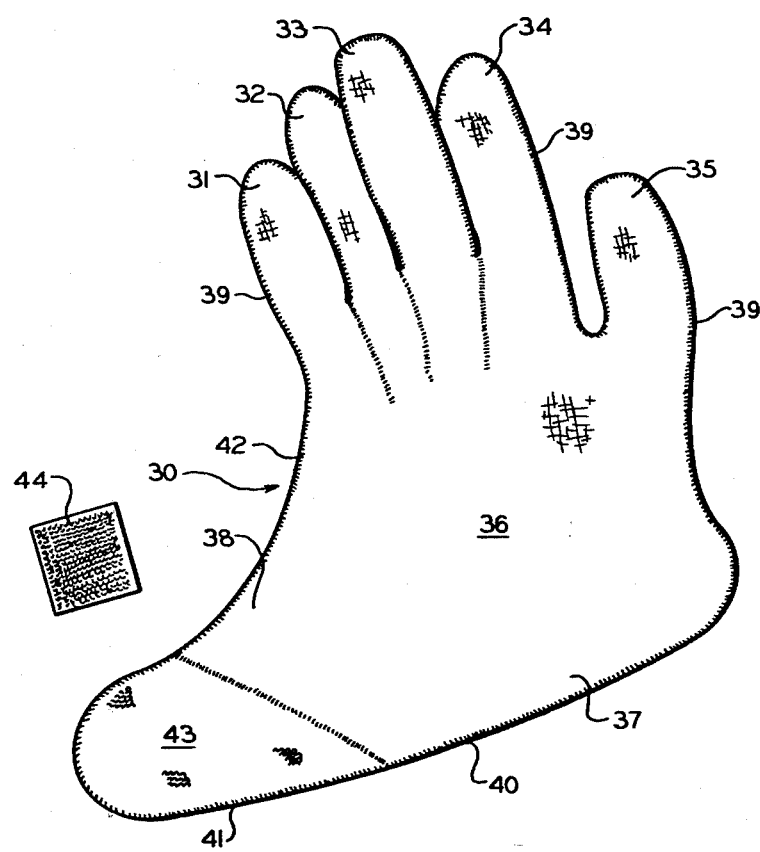
FIG. 3 is a plan view of an alternate embodiment of the present invention.

There is shown in FIG. 3 in plan view an alternate embodiment of a burn glove according to the present invention. A glove 30 includes finger portions 31, 32, 33, and 34 and a thumb portion 35 integral with a body portion 36. The body 36 tapers to a wrist portion 37 toward the thumb portion side and tapers into a flap 38 which extends at approximately right angles to the longitudinal axis of the finger portions. As in the glove 10, the glove 30 is formed from a pair of identical fabric blanks which are sewn together at the edges 39 thereof. The outside edges 40 of the wrist portion 37 are not sewn together to permit the insertion of a hand in the glove. However, these edges can be stitched to strengthen them.

The outside edges 41 of the flaps 38 also are not sewn together from the edges 40 of the wrist portion 37 to a point 42 along the edge of the body portion 36 near the finger portion 31. However, these edges can be stitched to strengthen them. As a hand is being inserted into the glove, the flaps 38 can be separated to open the body portion 36 for ease of entry.

The outer end of each flap 38 has a fastening means incorporated therein such as a piece of Velcro brand loop material 43. The flaps 38 are wrapped about the wrist in overlying fashion and secured together with a piece of double-sided Velcro brand hook material 44. Although other forms of fastening means could be utilized, the flaps and Velcro brand fastener have cost and ease of operation advantages over a zipper as well as the advantage of being able to adjust the tension applied at the wrist.

Figure 4:
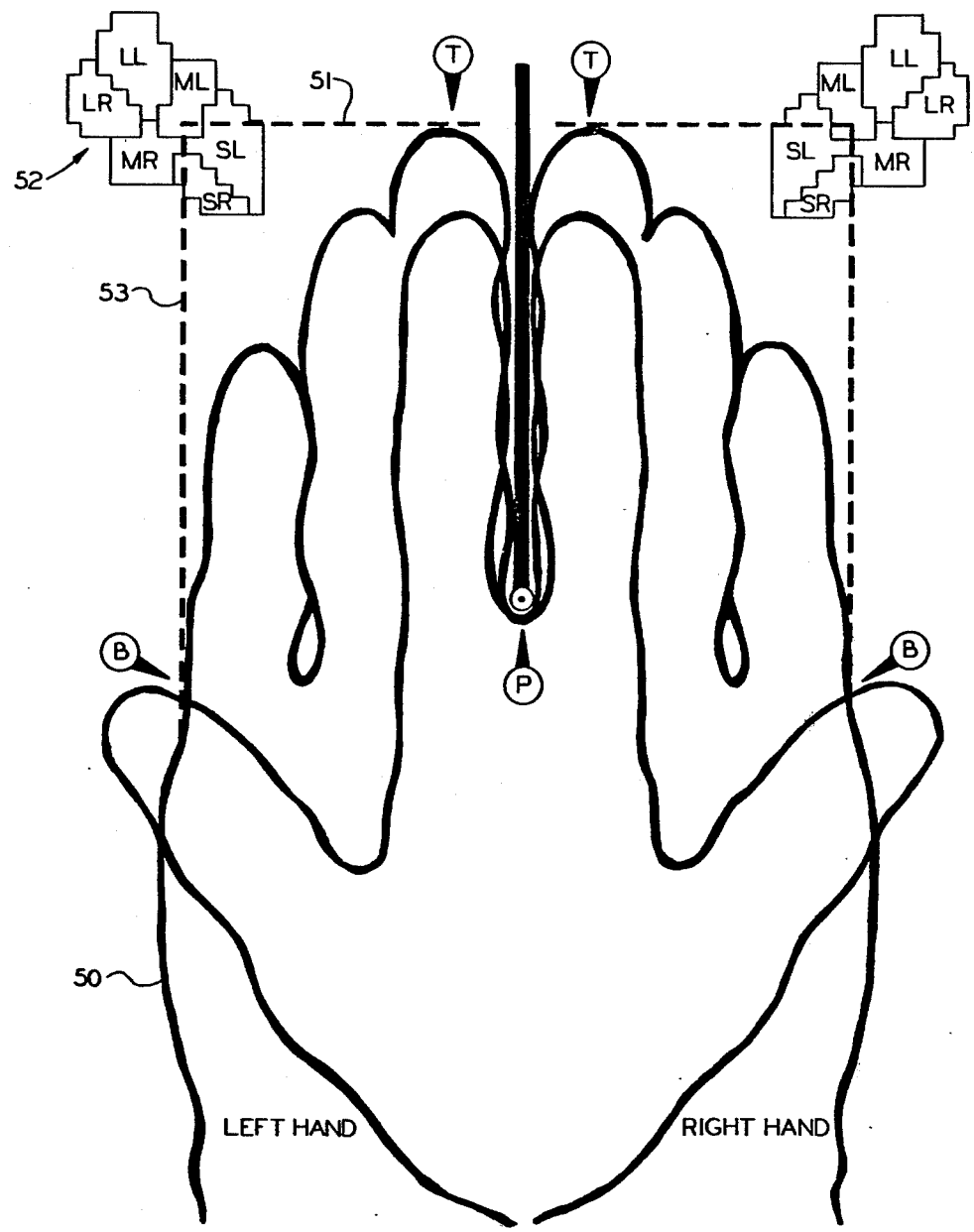
FIG. 4 is a measuring diagram for use in a method of determining the proper size glove according to the present invention.

Since it is a purpose of the present invention to provide a burn glove which is immediately available, the gloves must be manufactured in a limited number of standard sizes. There is shown in FIG. 4 a chart for use in a method of determining the proper standard size burn glove. The easiest measurements to make on a hand are from a two-dimensional profile. However, the volume of the hand must be considered when designing a glove since, not only must the hand fit into the glove, but the glove must fit so as to apply the desired amount of pressure.

Through the use of experimental techniques, various two dimensional and volume measurements were obtained from a population of hands. Statistical correlation coefficients were calculated and used to select the two dimensional measurement combination with the highest correlation to the hand volume. The data group was then divided into three equally populated hand volume subgroups or size ranges by equal subdivision of the area under the associated maximum likelihood normal probability curve. Points were plotted for each volume group at the intersections of the coordinates defined by the maximum correlation dimensions which in turn defined the chart areas allotted to each size. Further experimentation determined that the percentage of "misfits" was greatly reduced by dividing each volume size into two parts, a regular and a long for each.

The chart shown in FIG. 4 can be utilized for both the right and left hands. A pencil or similar object is centered on end at point P on the chart to function as a stop. A right hand 50 shown in outline form, is placed palm down with the web space between the middle and index fingers butted against the the stop at point P. The fingers on the hand are pressed together and a horizontal line 51 is traced from the tip T of the middle finger to a glove size diagram 52. Then a vertical line 53 is traced up from the base B of the little finger to the glove size diagram 52. The standard glove size will be indicated at the intersection of the vertical and horizontal lines which intersection will lie in one of the areas LL (large long), LR (large regular), ML (medium long), MR (medium regular, SL (small long), and SR (small regular).

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A method of selecting one a plurality of standard size burn gloves comprising the steps of:
   a. selecting a pair of two dimensional measurements which are correlated to hand volume;
   b. dividing a population of hand volumes into a predetermined number of approximately equally populated subgroup ranges;
   c. plotting two dimensional chart areas for each subgroup based upon intersections of said selected two dimensional measurements with reference to a predetermined point on the chart;
   d. assigning one of the standard sizes to each chart area;
   e. placing a hand on said predetermined point; and
   f. plotting the intersection of the pair of two dimensional measurements for said hand to select the proper standard glove size.

2. The method according to claim 1 wherein one of said two dimensional measurements extends from a base of a little finger of the hand to said chart areas.

3. The method according to claim 1 wherein one of said two dimensional measurements extends from a tip of a middle finger of the hand to said chart areas.

4. The method according to claim 1 wherein said steps c. and d. are performed for both right and left hands.

5. The method according to claim 1 wherein step e. is performed by placing the hand palm down on said predetermined point.

6. The method according to claim 1 wherein said predetermined point abuts a web area between a middle finger and an index finger of the hand.

* * * * *